(12) United States Patent
Bettinelli et al.

(10) Patent No.: US 9,475,657 B2
(45) Date of Patent: Oct. 25, 2016

(54) APPARATUS AND PROCESS FOR TRANSFERING AND ROTATING AN OBJECT

(71) Applicant: INMAN S.R.L., Milan (IT)

(72) Inventors: Vincenzo Bettinelli, Crema (IT); Gianfranco Colombo, Bergamo (IT)

(73) Assignee: INMAN S.R.L., Milan (IT)

( * ) Notice: Subject to any disclaimer, the term of this patent is extended or adjusted under 35 U.S.C. 154(b) by 0 days.

(21) Appl. No.: 14/783,167

(22) PCT Filed: Apr. 10, 2013

(86) PCT No.: PCT/IB2013/000639
§ 371 (c)(1),
(2) Date: Oct. 8, 2015

(87) PCT Pub. No.: WO2014/167369
PCT Pub. Date: Oct. 16, 2014

(65) Prior Publication Data
US 2016/0031654 A1  Feb. 4, 2016

(51) Int. Cl.
  *B65G 47/84* (2006.01)
  *A61F 13/15* (2006.01)
  *B65G 29/00* (2006.01)
  *F16H 25/16* (2006.01)

(52) U.S. Cl.
  CPC ....... *B65G 47/846* (2013.01); *A61F 13/15764* (2013.01); *B65G 29/00* (2013.01); *B65G 47/848* (2013.01); *F16H 25/16* (2013.01)

(58) Field of Classification Search
  CPC .. B65G 29/00; B65G 47/846; B65G 47/847; B65G 47/848
  See application file for complete search history.

(56) References Cited

U.S. PATENT DOCUMENTS

| 4,574,022 A | 3/1986 | Johnson et al. |
| 5,025,910 A | 6/1991 | Lasure et al. |
| 6,722,494 B2 * | 4/2004 | Nakakado ......... A61F 13/15764 198/377.01 |
| 7,543,697 B2 | 6/2009 | Legallais |
| 8,011,493 B2 * | 9/2011 | Giuliani ............... B65G 47/244 198/406 |
| 8,607,959 B2 * | 12/2013 | Papsdorf ........... A61F 13/15764 198/377.04 |

FOREIGN PATENT DOCUMENTS

EP  1820757 A1  8/2007

OTHER PUBLICATIONS

International Search Report based on International Application No. PCT/IB2013/00639.

* cited by examiner

*Primary Examiner* — Gene Crawford
*Assistant Examiner* — Keith R Campbell
(74) *Attorney, Agent, or Firm* — Lucas & Mercanti, LLP

(57) ABSTRACT

Apparatus for transferring an object from a first station to a second station with a different orientation is provided comprising a stator, a rotor rotatable externally of the stator about an axis of rotation, and at least one retaining member for retaining the object. The retaining member can rotate integrally with the rotor, and is rotatable with respect to the rotor about its own axis of rotation. The stator has a cam profile coupled to and functionally cooperating with at least one axially extending follower which is constrained to the retaining member. The axis of rotation of the retaining member and the axis of extension of the follower are substantially always incident to the axis of rotation of the rotor.

13 Claims, 7 Drawing Sheets

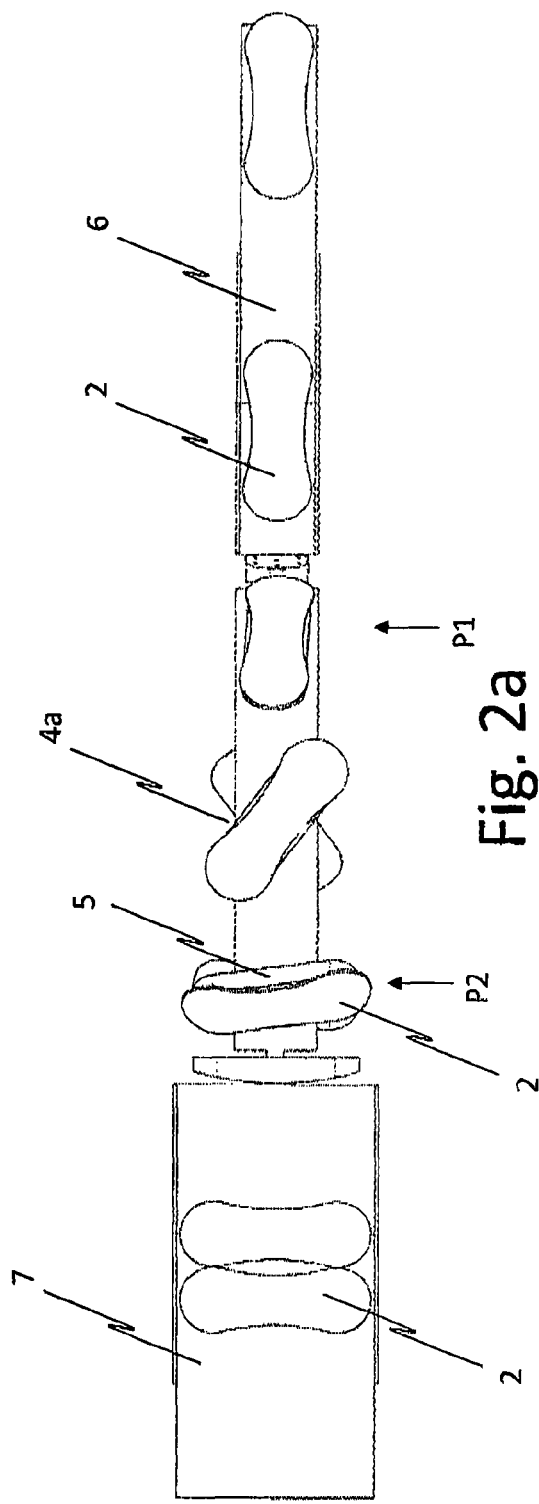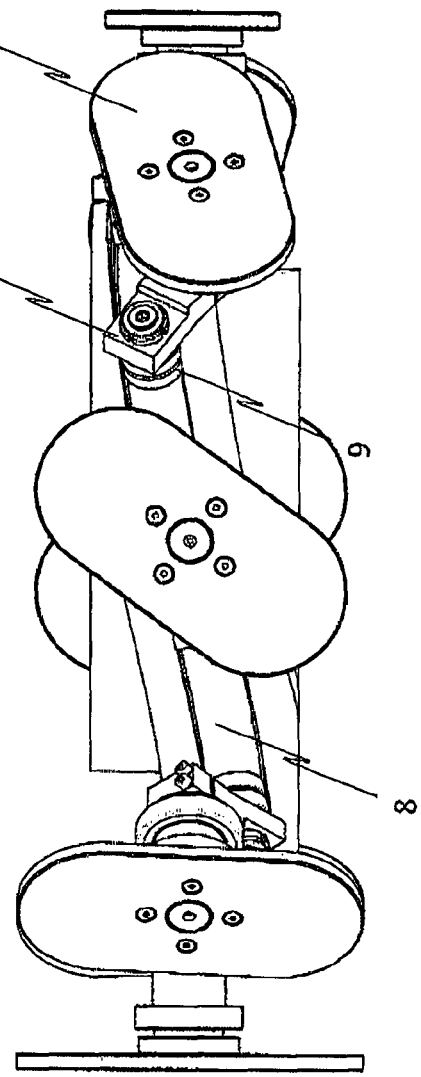

APPARATUS AND PROCESS FOR TRANSFERING AND ROTATING AN OBJECT

CROSS-REFERENCE TO RELATED APPLICATIONS

This application is a 371 of PCT/IB2013/000639, filed Apr. 10, 2013.

TECHNICAL FIELD

The following invention relates to the field of apparatuses intended to transfer objects, preferably medium or small-sized objects, between two operating stations, as well as to change the orientation of the object from one station to the other.

BACKGROUND OF THE INVENTION

Such apparatuses, which are known in the art, comprise one or more retaining members intended to retain and transport the object to and from the two stations and also able to rotate the object while the latter is transported.

These retaining members, for example consisting of supports provided with either mechanical gripping means or suction means, are generally rotationally driven along a path connecting the two stations between which the objects have to be transferred, and they are further rotationally driven about their own axis of rotation which is usually orthogonal to the gripping surface of the respective support.

Although it is possible to provide electrically-operated retaining members able to rotate the object, it is conventional to use purely mechanical devices which are configured to control the rotation of the afore said retaining members about their own axis of rotation because such devices are more reliable and cost-effective.

Typically, in order to rotate the retaining members about their own axis, cam-and-follower devices are used in which the retaining members are operatively associated with a follower running along a path determined by a cam profile.

Particularly, a handling apparatus of the above referred type is known in which the retaining members for retaining the object to be transferred are constrained to a rotor which is rotatable about a respective stator in such a way that the retaining members are forced to follow the rotor in its revolving movement about the stator itself while being able to rotate about themselves, about their own axis of rotation.

The rotation of each retaining member about its own axis is controlled by a respective follower which is connected, either directly or indirectly, to the axis of rotation of the retaining member—for example via a lever—and which engages and functionally cooperates with a cam formed on the same stator. Thus, the displacement of the follower along the cam profile determines a controlled rotation of the retaining member to which it is constrained.

Although these devices have proven to be more reliable and cost-effective than, for example, electrically-operated retaining members, however the frictions generated between the cam profile and the follower result in a decreased speed of the retaining members and, therefore, in a reduced performance of the device.

Moreover, these frictions cause a not negligible wear of the parts, resulting in a need for a periodic maintenance and possible replacement thereof.

Finally, given the variable nature of coupling between the follower constrained to the rotor and the cam formed on the stator, jams and malfunctions may not be excluded.

Therefore, an aim of the present invention is to provide an apparatus for transferring and rotating an object which is operatively faster than those of the prior art and which reduces the potential occurrence of jams or malfunctions.

Another aim of the present invention is to provide a transferring apparatus of the above referred type which requires less maintenance compared to the devices known in the art.

A further aim of the present invention is to provide an apparatus for transferring and rotating an object whose components have a longer operating life compared to the prior art.

SUMMARY OF THE INVENTION

These and other aims are achieved by the present invention by means of an apparatus for transferring an object from a first station to a second station with a different orientation compared to that at the first station, comprising a stator, a rotor rotatable externally of the stator about an axis of rotation, and at least one retaining member for retaining the object, the retaining member being rotatable integrally with the afore said rotor with respect to the stator and being in turn rotatable with respect to the rotor about an own axis of rotation. Furthermore, the afore said stator is provided with a cam profile coupled to and functionally cooperating with at least one axially extending follower, wherein such a follower is constrained to a respective retaining member—i.e. it is functionally connected, either directly or indirectly, to the axis of rotation of the retaining member—in such a way as to cause said retaining member to be rotated about its axis of rotation as a function of the relative position of the follower with respect to the cam profile. Advantageously, the axis of rotation of the retaining member and the axis of extension of the follower are always substantially incident to the axis of rotation of the rotor.

Preferably, according to a preferred aspect of the present invention, the axis of rotation of the above mentioned retaining member and the axis of extension of the follower are always substantially incident to each other and, even more preferably, they are always substantially incident to each other at their point of incidence to the axis of rotation of the rotor.

Furthermore, according to another preferred aspect of the present invention, the axis of rotation of the above mentioned retaining member and/or the axis of extension of the follower are always substantially radial with respect to the above mentioned axis of rotation of the rotor.

Note that, here and below, the term "axially extending follower" means any mechanical member which is in a holonomic constraint relationship with a cam profile and whose shape is such that the sliding of the follower along the cam profile substantially results in a displacement of the follower which is substantially either orthogonal or parallel to such an axis. In this specific case, however, given the constraint existing between the follower and the retaining member, in order to allow the rotation of the latter to be controlled by the follower, it is understood that the axially-extending follower will be forced to move only along directions which are substantially orthogonal to such an axis of extension in its constrained motion along the cam profile.

Note also that, as known by the field technician, the arrangement in which the follower is constrained to the respective retaining member—i.e. it is functionally connected, either directly or indirectly, to the axis of rotation of the retaining member—in such a way as to cause the retaining member to be rotated about its own axis of rotation as a function of its relative position with respect to the cam profile, can be differently implemented, for example with the use of a "L"-shaped lever, and it is quite common in the field of the present invention.

Due to the particular configuration of both the follower and the axis of rotation of the retaining member, i.e. their orientation with respect to the axis of rotation of the rotor as described above, the undue wiping—and thus the friction—between the apparatus parts are minimized.

Particularly, since the transmission of forces between the follower and the cam in the lateral direction with respect to the direction of the path of the follower is reduced, the friction between the two members is minimized.

Obviously, a reduced friction between the various members allows the apparatus to operate at an increased speed while decreasing the wear of parts compared to the arrangements known in the art.

According to an aspect of the present invention, the stator has a tapered cylindrical shape.

This stator shape allows the path of the cam profile to be "wound" around the stator according to an optimal configuration.

According to an aspect of the present invention, the rotor has an annular shape.

According to an aspect of the present invention, the cam profile is formed as a groove along at least one side surface of said stator. Such an arrangement is the simplest and most cost-effective to be produced, but other different configurations, e.g. a cam profile formed as a rail, are not excluded.

According to an aspect of the present invention, the retaining member comprises a retaining head adapted to cooperate with the object to be handled, and a shaft extending along the above said axis of rotation of the retaining member and adapted to rotationally cooperate with the rotor. The retaining head is constrained to a first end of the shaft, and the follower is constrained to a second end of the shaft by means of a suitable connection such as, for example, a lever-type connection.

According to another aspect of the present invention, the retaining head has means for reversibly fastening the object. Typically, these means are formed as air-suction means.

According to a further aspect of the present invention, the connection has at least two portions which are tilted to each another. Such an arrangement allows the path of the follower along the cam profile of the stator to be optimized and, particularly, it is the simplest approach to make the axis of extension of the follower and the axis of rotation of the retaining members to be incident to each other. Indeed, it is clear that if these axes were parallel, the peculiar feature of the present invention that both these axes are directed towards the axis of rotation of the stator could be not satisfied.

According to an aspect of the present invention, the follower has a substantially cylindrical shape.

The present invention also relates to a process for transferring an object while simultaneously changing the orientation thereof by means of an apparatus of the above referred type.

BRIEF DESCRIPTION OF THE FIGURES

Exemplary and not limiting embodiments of the present invention are now illustrated with reference to the figures, in which:

FIG. 2a is a top view of the apparatus of FIG. 1 when operating;

FIG. 2b is a detailed top view of the apparatus of FIG. 1;

DETAILED DESCRIPTION OF THE INVENTION

Figure 1:
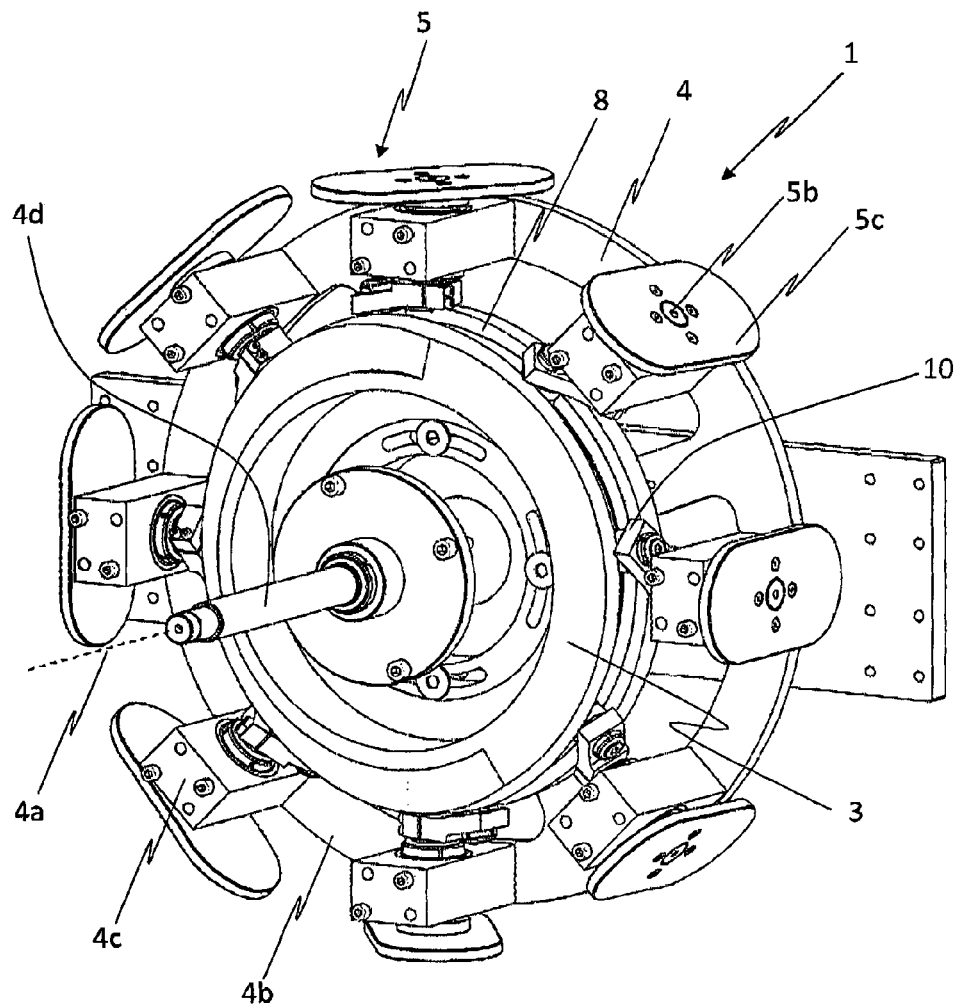
FIG. 1 is a perspective view of a first embodiment of an apparatus according to the present invention.

Referring to the figures appended hereto, an apparatus 1 for transferring an object 2 according to the present invention comprises a stator 3, a rotor 4 rotatable externally of the stator 3 about an axis of rotation 4a, and at least one retaining member 5 for retaining the object 2. Particularly, as can be seen from FIG. 2, the apparatus 1 allows the object 2 to be transferred from a first station 6 to a second station 7 and at the same time to change the orientation of the object 2.

In FIG. 1 there is shown an apparatus 1 having eight retaining members 5, although a different number of retaining members, even one retaining member, may be used. The retaining members 5 are rotatable integrally with the rotor 4 with respect to the stator 3, and they are in turn rotatable with respect to the rotor 3. These two degrees of freedom allow the apparatus to transfer the object 2 between two stations 6 and 7, by a revolving movement of the retaining members 5 about the axis 4a of the stator 4, while simultaneously allowing the object to be rotated by a rotational movement of each retaining member 5 about its own axis of rotation 5a.

From an analysis of FIG. 2, it is possible to note that the apparatus 1 is particularly suitable for transferring and rotating objects which are light in weight and reduced in size, for example diapers.

From FIG. 1 it is also possible to understand the various positions of each retaining member 5 during its rotation integrally with the rotor 4 about the stator 3.

Figure 4:
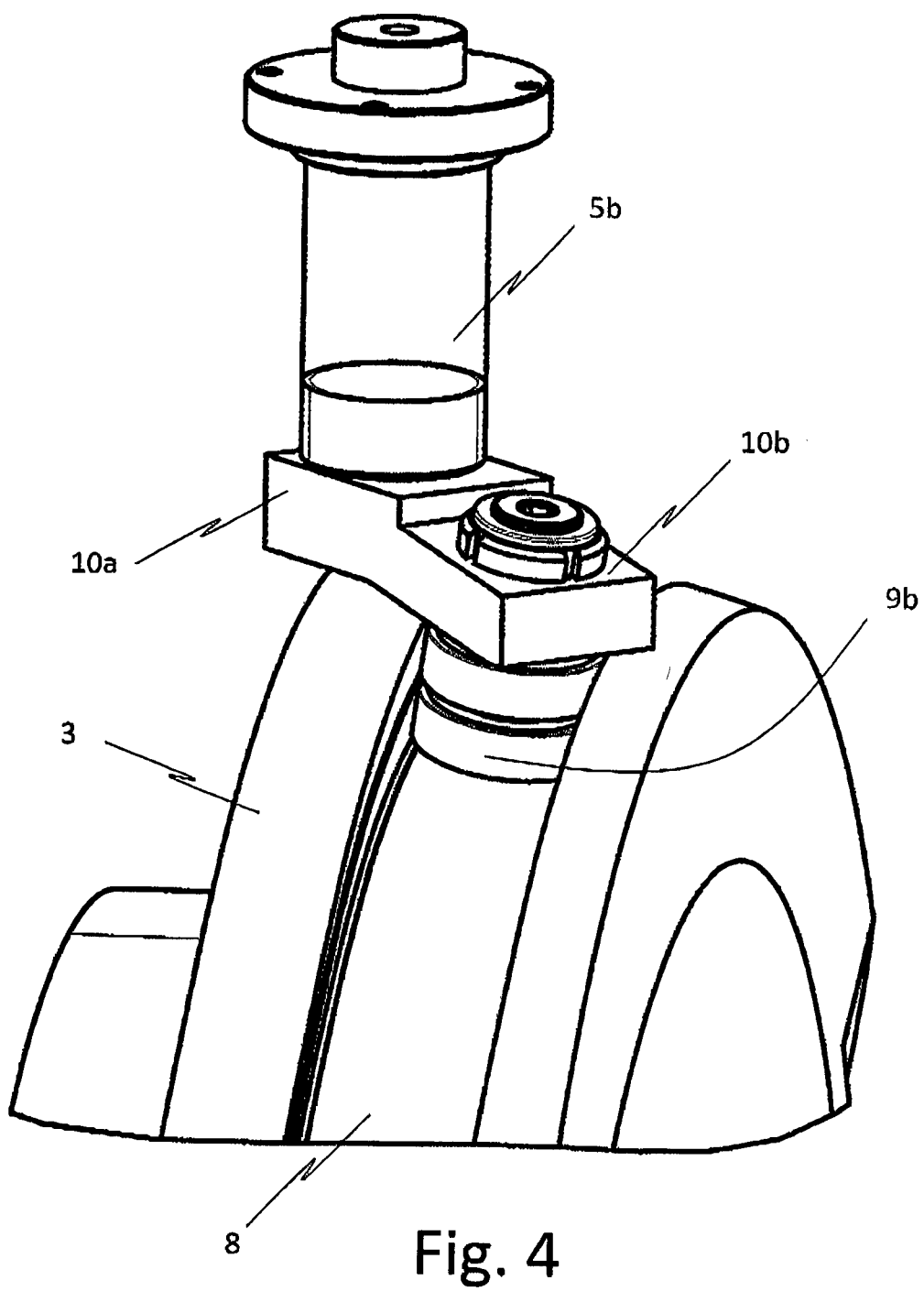
FIGS. 4 and 5 are detailed views of the cam-and-follower system of the apparatus of FIG. 1.
Figure 5:
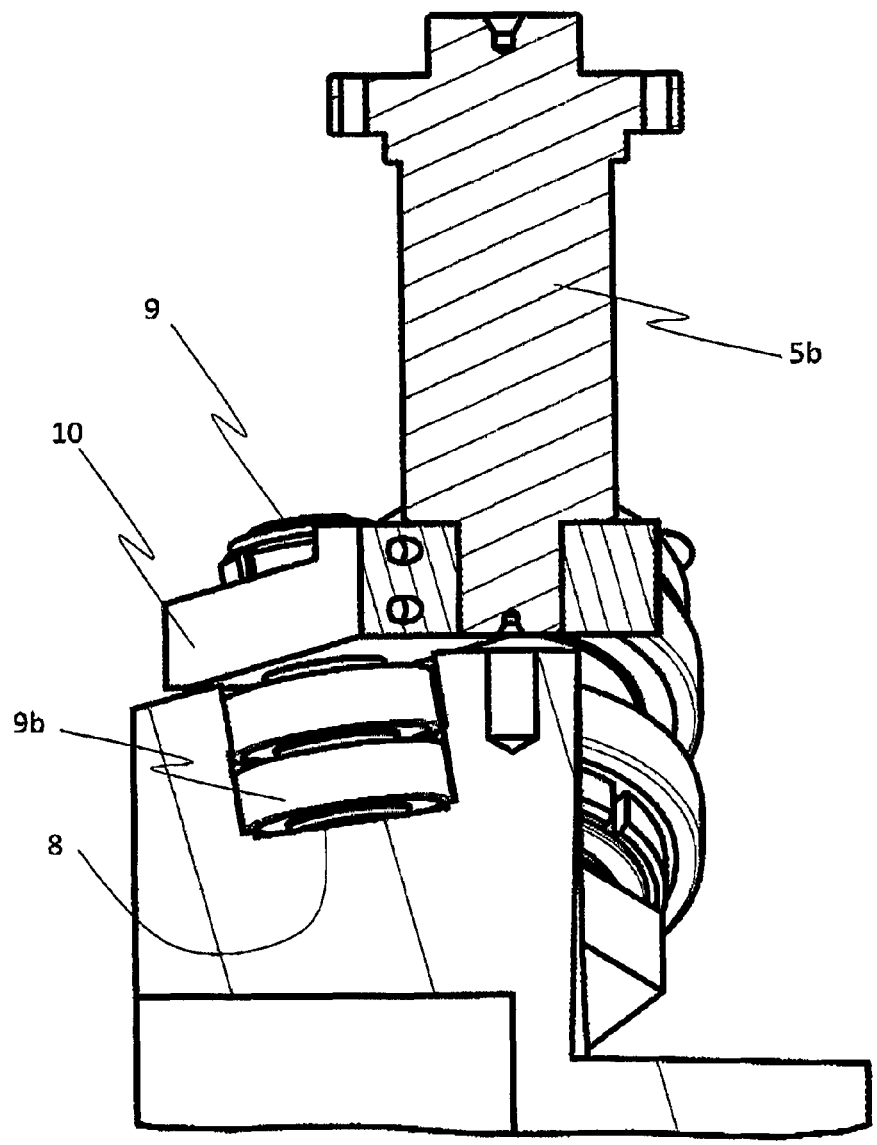

In order to cause a relative rotation between the rotor 4 and the retaining members 5, the stator 3 is provided with a cam profile 8 cooperating with axially extending followers 9. Each retaining member 5 is operatively constrained to a follower 9 via connecting means 10 which can be seen in detail in FIGS. 4 and 5.

In other words, the follower 9, which therefore extends along an axis 9a, is functionally connected to the axis of rotation 5a of the retaining member 5 via connecting means 10, substantially comprising a lever, in such a way that each displacement of the follower 9 itself along the cam profile 8 results in a corresponding rotation of the retaining member 5 about its own axis of rotation 5a.

Figure 3:
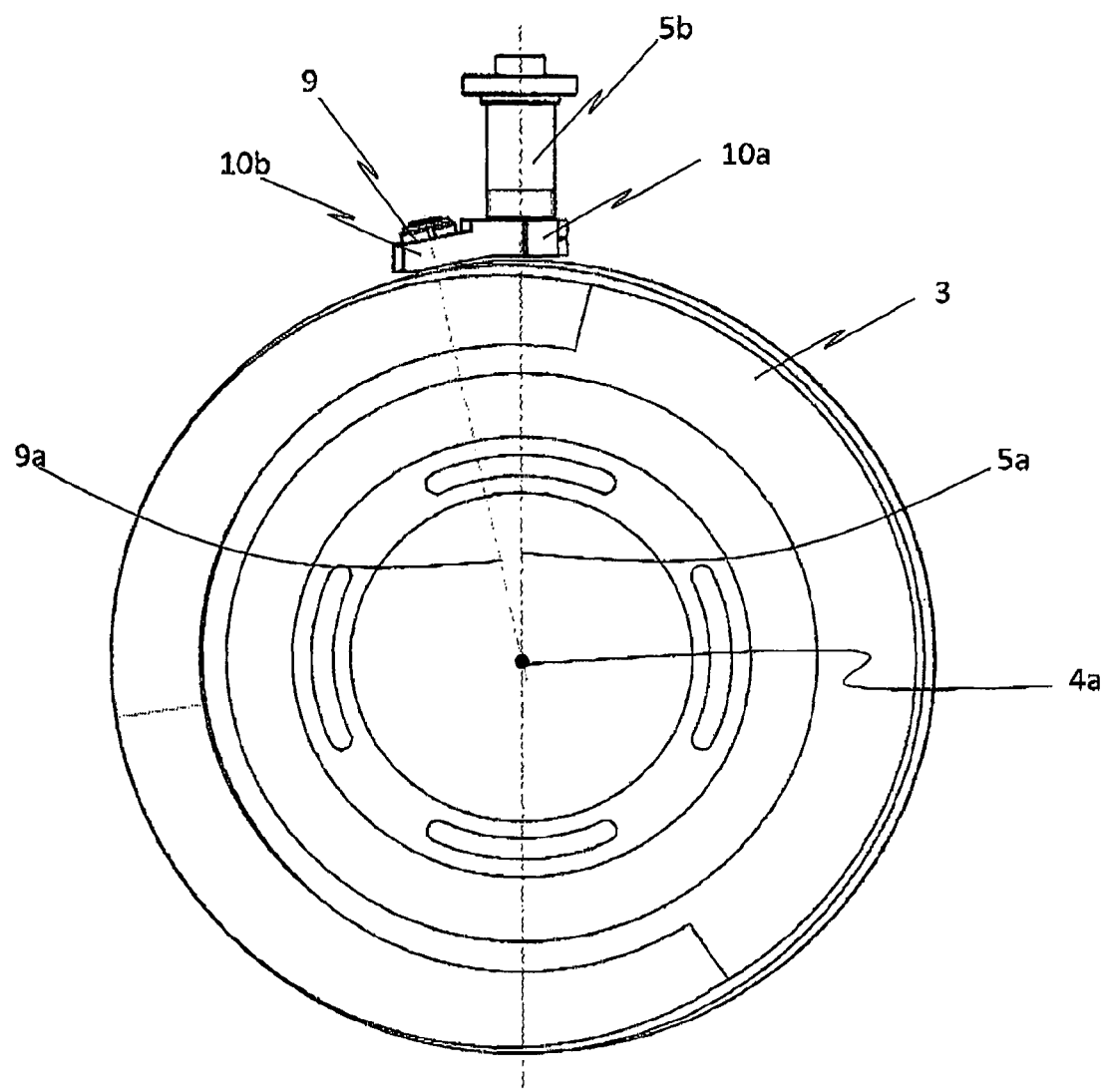
FIG. 3 is a front partial view of the apparatus of FIG. 1.
Figure 7:
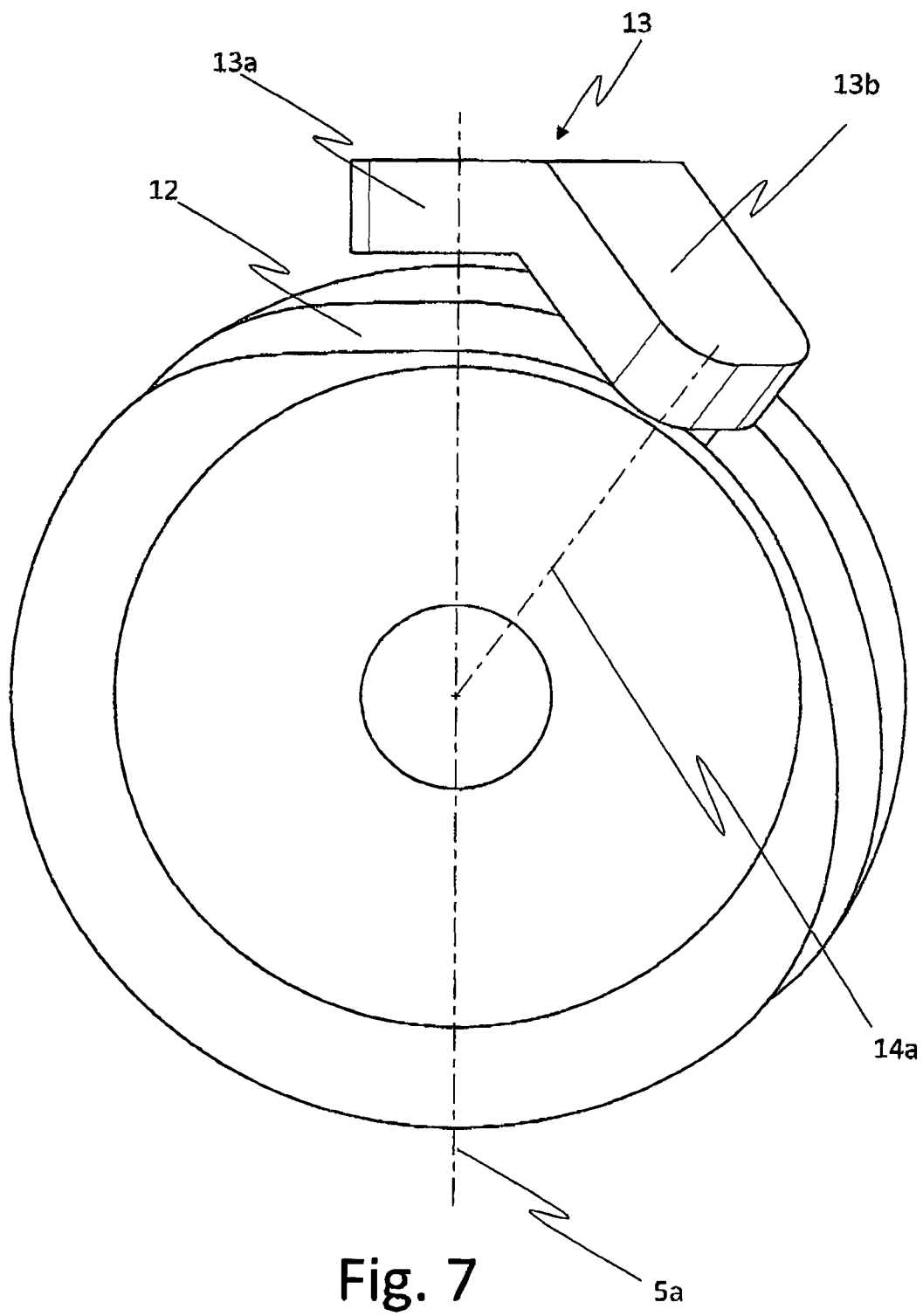

Advantageously, as can be seen for example from FIG. 3 or 7 appended hereto, both the axis of rotation 5a of each retaining member 5 and the axis of extension 9a of the corresponding follower 9a are always substantially incident to the axis of rotation 4a of the rotor 4, and preferably they are incident to each other, and even more preferably they are incident to each other at their point of incidence to the afore said axis of rotation 4a of the rotor 4.

According to another preferred aspect of the present invention, the above said axes 9a, 5a, i.e. the axis of extension of the follower 9 and the axis of rotation of the retaining member 5, respectively, are arranged in such a way as to be substantially always radial with respect to the axis of rotation 4a of the rotor 4.

As will be better discussed below, such a result is achieved due to the particular shape of the retaining members 5 and/or of the afore said connecting means 10 and/or of the followers 9, which is designed in such a way as to maintain the axis 9a of the follower 9 and the axis 5a of the retaining member 5 always substantially incident, and preferably also radial, to the axis of rotation 4a of the rotor 4.

The stator 3 is shaped as a cylindrical member which, in the embodiment of FIG. 1, is limited in height. The cam profile 8 is embodied by a groove running along the side surface and, therefore, such a groove will be hereinafter referred to by the same reference numeral as that of the cam profile 8. As can be seen from FIG. 1, and as more clearly observed from the embodiment of FIGS. 6 and 7, the side surface of the stator 3 is preferably tapered, and it has a diameter which is increased substantially at the center line.

Particularly, in the embodiments shown herein, the stator 3 is tapered in such a way to be shaped as a sphere portion. This shape has been found to be particularly advantageous for implementing the path of the cam profile 8 along the stator 3.

The groove 8 runs along the side surface of the stator 3 so as to be wind the stator 3 while varying its height with respect to the cylindrical body of the stator 3 itself, thus following a path substantially sinusoidal.

The rotor 4 comprises an annular body 4b connected to and rotatable about a pin 4d, and coupling members 4c, 4b protruding from the annular body 4b and adapted to cooperate with the retaining members 5. In the embodiment shown herein, the coupling members 4c are parallelepiped-like blocks having a through-opening adapted to receive a shaft 5b of the retaining members 5 so as to maintain the axis 5a of the shaft 5b substantially always directed towards the axis of rotation 4a of the rotor 4.

The retaining members comprises a retaining head 5c configured so as to be able to cooperate with the object 2. Generally, as in the embodiment shown herein, the retaining head is flat in shape and complementary to the object 2. The object 2 is picked up from and dropped to the stations 6 and 7 by known devices, for example air-suction means. The retaining members further comprise a shaft 5b rotatable within the above described opening of the coupling members 4c. The retaining head 5c is located at one end of the shaft 5b, whereas the connecting means 10 are located at the second end of the shaft 5b, being rotatable integrally with the shaft 5b too. In the embodiment shown herein, the connecting means comprise two preferably planar portions 10a and 10b which are tilted to each other, and in which a first portion 10a has an opening for the shaft 5b of the retaining members 5, and a second portion 10b has an opening for the follower 9. As anticipated herein, the first portion 10a retains the shaft 5b securely to prevent the two members from rotating with respect to each other. The use of a number of portions greater than two is not excluded. The follower 9 can be constrained either with clearance and/or with the use of bearings within the respective opening of the second portion 10b so as to permit a rotation between the two members, otherwise it can be made integral with the connecting means 10. In the embodiment of FIGS. 1-5, the follower 9 and the connecting means 10 can be rotated with respect to each other.

The follower 9 is shaped as an axially extending body or at least comprises an axially extending body to which the connecting means are connected, and such a body has an axis of extension 9a which is directed towards the axis of rotation 4a of the rotor 4. This feature is maintained substantially throughout the whole path of the follower within the groove 8.

In the embodiment of FIGS. 1-5, the follower has coupling rings 9b for the coupling to the side edges of the groove 8.

Figure 6:
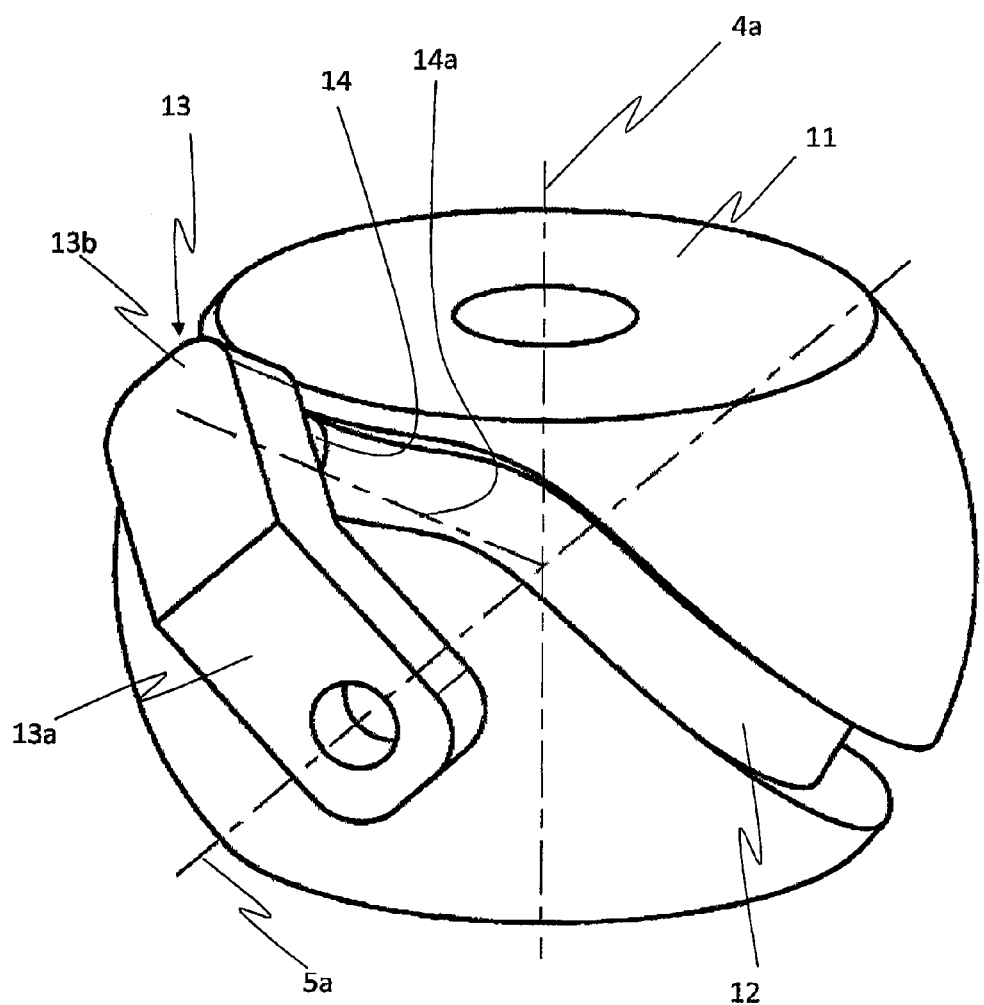
FIGS. 6 and 7 are detailed views of the cam-and-follower system of an apparatus according to an alternative embodiment of the present invention.

A further embodiment of the present invention is shown in FIGS. 6 and 7. The members not shown herein are to be considered similar to those of the embodiment of FIGS. 1-5.

The three dimensions of the stator 11 are similar to each other, and the stator is shaped as a cylinder with an increased taper as compared to that of the previous embodiment.

Consequently, also the deformation of the path of the groove 12 is more prominent, the deformation being considered with reference to a hypothetical circular path of the groove about the stator 11.

The connecting means 13 have two portions 13a and 13b which are similar to the previously described portions 10a and 10b.

However, unlike the previously described embodiment, the portion 13a has a follower 14 which is integral and preferably unitary with the portion itself. Herein, the follower 14 is shaped as a substantially cylindrical body.

Also in this embodiment it is possible to observe the peculiar feature of the invention whereby both the axis of rotation 5a of the retaining members and the axis of extension 14a of the follower 14 are directed towards the axis of rotation 4a of the rotor 4.

As anticipated above, this arrangement enables to reduce stresses and frictions along non-radial directions with respect to the axis of rotation 4a of the rotor 4, thereby actually increasing the efficiency of the apparatus 1.

Additional embodiments of the cam profile, follower and connecting means are possible.

For example, it is possible to shape the cam profile as a rail and the respective follower as a slider having a typically cylindrical axial body to which connecting means are connected, having an axis of extension which is also directed towards the axis of rotation of the rotor. Furthermore, the slider may be replaced with a set of rollers or wheels adapted to cooperate with the rail or a similar cam profile.

Generally, the protection scope of the present invention embraces a generic follower with a respective cam profile, the follower having an axial body which is oriented towards the axis of rotation of the rotor throughout substantially the whole travel thereof along the cam profile.

Additionally, the definitions given in the preamble of the independent claims encompass various embodiments of the rotor, the stator and the retaining members other than those shown and known in the art, and they equally fall within the protection scope of the present invention.

In the light of the above description, and with particular reference to FIG. 2, the process of an apparatus according to the present invention becomes apparent to a field technician.

The process described below refers to a diaper as the object 2 to be transferred, although it is understood that the apparatus of the present invention can be used to transfer other objects, particularly objects which are small in size and/or light in weight.

A diaper 2 is picked up by a retaining member 5 from a first station 6 according to known methods. In the embodiment shown herein, the retaining head 5c is provided with air vents adapted to generate a negative pressure at the surface of the head 5c so as to attract and retain the object. The successive positions of the retaining member 5 are sequentially visible in FIG. 2 because they correspond in sequence to the positions occupied by the other shown retaining members 5. Particularly, while the rotor 4 and thus the retaining members 5 are being rotated about the axis of rotation 4a, the engagement of the follower 9, 14 within the cam profile 8, 12 causes the retaining members 5 to be rotated, thereby changing the orientation of the diaper 2 from a first position P1 to a second position P2. After a further rotation of the rotor 4, the diaper 2 is dropped by the retaining members 5 at the second station 7 according to the orientation achieved in the second position P2.

The interaction of the cam profile 8, 12 with the follower 9, 14 can be more easily understood when considering FIG. 2b and figures related to the second embodiment, as the path deformation of the cam profile 12 is more evident than that in the first embodiment; however, the process described below is equally applied to both the embodiments.

Particularly, the connecting means 10, 13 are rotatable integrally with the retaining members 5 about the axis 4a. During such a rotation, the follower 9, 14 covers the profile of the cam profile 8, 12. The change in direction of the path of the cam profile 8, 12 causes a relative rotation of the connecting means, and thus of the retaining members 5, about the axis of rotation 5a. Therefore, the movement of the retaining members 5 is the result of two components, i.e. a rotational movement about the axis of rotation 4a of the rotor 4 and a rotational movement about the axis of rotation 5a.

As described above, the axis of rotation 5a of the retaining member 5 and the axis of extension 9a, 14a of the follower 9, 14 are always substantially incident and preferably radial to the axis of rotation 4a of the rotor 4, thereby minimizing the frictions between the various parts of the apparatus 1.

The invention claimed is:

1. Apparatus for transferring an object from a first station to a second station with a different orientation compared to that at said first station, comprising a stator, a rotor rotatable externally of said stator about an axis of rotation of the rotor, and at least one retaining member for retaining said object,
   said at least one retaining member being rotatable integrally with said rotor with respect to said stator and being in turn rotatable with respect to said rotor about an axis of rotation of said at least one retaining member,
   wherein said stator is provided with a cam profile coupled to and functionally cooperating with at least one axially extending follower,
   said at least one follower being constrained to said at least one retaining member in such a way as to cause said at least one retaining member to be rotated about said axis of rotation of said at least one retaining member as a function of the relative position of said follower with respect to said cam profile,
   wherein said axis of rotation of said at least one retaining member and the axis of extension of said follower are substantially always incident to said axis of rotation of the rotor.

2. Apparatus according to claim 1, wherein said axis of rotation of said retaining members and said axis of extension of said follower are substantially incident to each other.

3. Apparatus according to claim 1, wherein said axis of rotation of said retaining members and said axis of extension of said follower are substantially incident to each other at the point of incidence to said axis of rotation of the rotor.

4. Apparatus according to claim 1, wherein the axis of rotation of said retaining member and/ or the axis of extension of the follower is/ are substantially always radial with respect to said axis of rotation of the rotor.

5. Apparatus according to claim 1, wherein said stator has a tapered cylindrical shape.

6. Apparatus according to any claim 1, wherein said rotor has an annular configuration.

7. Apparatus according to claim 1, wherein said cam profile is formed as a groove running along at least one side surface of said stator.

8. Apparatus according to claim 1, wherein said retaining member comprises a retaining head adapted to cooperate with said object, a shaft adapted to rotationally cooperate with said rotor and extending along said axis of rotation of the retaining member, said retaining head being constrained to a first end of said shaft and said follower being constrained, either directly or indirectly, to a second end of said shaft.

9. Apparatus according to claim 8, wherein said retaining head is provided with fastening means for reversibly fastening said object.

10. Apparatus according to claim 1, wherein said follower is constrained to said retaining member by a connection having at least two portions which are tilted to each another.

11. Apparatus according to claim 1, wherein said follower is substantially cylindrical in shape.

12. Process for transferring an object from a first station to a second station while simultaneously changing the orientation thereof by means of an apparatus comprising a stator, a rotor rotatable externally of said stator about an axis of rotation of the rotor, and at least one retaining member for retaining said object,
   said at least one retaining member being rotatable integrally with said rotor with respect to said stator and being in turn rotatable with respect to said rotor about an axis of rotation of said at least one retaining member,
   wherein said stator is provided with a cam profile coupled to and functionally cooperating with at least one axially extending follower,
   said at least one follower being constrained to said at least one retaining member in such a way as to cause said at least one retaining member to be rotated about said axis of rotation of said at least one retaining member as a function of the relative position of said follower with respect to said cam profile said process comprising:
   a. picking up said object from said first station by means of said retaining member;
   b. rotating said rotor with respect to said stator, said follower cooperating with said cam profile in such a way as to cause a relative rotation of said retaining members with respect to said rotor; and
   c. dropping said object at said second station;
   said axis of said follower and said axis of said at least one retaining member in said steps a, b and c being always substantially arranged incident to said axis of rotation of said rotor.

13. Process according to claim 12, wherein said axis of said follower and said axis of said at least one retaining member are always substantially radial with respect to said axis of rotation of said rotor.

* * * * *